(12) United States Patent
Hung

(10) Patent No.: US 8,870,573 B2
(45) Date of Patent: *Oct. 28, 2014

(54) DENTAL IMPLANT

(76) Inventor: William Y. S. Hung, Claremont, CA (US)

(*) Notice: Subject to any disclaimer, the term of this patent is extended or adjusted under 35 U.S.C. 154(b) by 290 days.

This patent is subject to a terminal disclaimer.

(21) Appl. No.: 12/755,210

(22) Filed: Apr. 6, 2010

(65) Prior Publication Data

US 2011/0244427 A1 Oct. 6, 2011

(51) Int. Cl.
*A61C 8/00* (2006.01)

(52) U.S. Cl.
CPC .............. *A61C 8/0022* (2013.01); *A61C 8/006* (2013.01); *A61C 8/0039* (2013.01); *A61C 8/0068* (2013.01); *A61C 8/0089* (2013.01); *A61C 8/0092* (2013.01)
USPC .......................................................... 433/174

(58) Field of Classification Search
USPC .............. 433/172, 173, 174, 175, 176, 201.1, 433/202.1, 215, 220, 221
See application file for complete search history.

(56) References Cited

U.S. PATENT DOCUMENTS

| | | | | |
|---|---|---|---|---|
| 4,854,873 A | * | 8/1989 | Linden | 433/173 |
| 5,087,199 A | * | 2/1992 | Lazarof | 433/173 |
| 5,433,606 A | * | 7/1995 | Niznick et al. | 433/173 |
| 5,989,027 A | * | 11/1999 | Wagner et al. | 433/173 |
| 6,655,962 B1 | * | 12/2003 | Kennard | 433/174 |
| 2004/0006346 A1 | * | 1/2004 | Holmen et al. | 606/73 |
| 2005/0037319 A1 | * | 2/2005 | Bulard et al. | 433/173 |
| 2005/0164146 A1 | * | 7/2005 | Cantor | 433/173 |
| 2006/0003290 A1 | * | 1/2006 | Niznick | 433/174 |
| 2007/0037123 A1 | * | 2/2007 | Mansueto et al. | 433/173 |
| 2007/0292820 A1 | * | 12/2007 | Canter | 433/173 |
| 2008/0081316 A1 | * | 4/2008 | Chung | 433/174 |
| 2008/0113316 A1 | * | 5/2008 | Menke | 433/174 |
| 2008/0241791 A1 | * | 10/2008 | Bulard et al. | 433/174 |
| 2009/0305191 A1 | * | 12/2009 | Jandali | 433/174 |

* cited by examiner

*Primary Examiner* — Cris L Rodriguez
*Assistant Examiner* — Justin O'Donnell
(74) *Attorney, Agent, or Firm* — Raymond Y. Chan; David and Raymond Patent Firm

(57) ABSTRACT

In order to further facilitate the insertion of the dental implant into the bone, 3 plurality of apex indentations 13 are spacedly formed in the insertion root portion of the dental implant body 10. Referring to FIGS. 1 to 3 of the drawings, in a preferred embodiment of the present invention, each apex indentation 13 has a V-shape cross section defining two blade surfaces 131 cutting into the dental implant body 10 from the tip of the first end 11 of the dental implant body 10. At these two blade surfaces 131, the cross section of the asymmetric thread 20 is exposed and the blade edge 23 of the asymmetric thread 20 forms one or more cutting blades 24, wherein the dental implant of the present invention is screwed in the bone, the cutting blades 24 are the first part to cut into the bone. If the bone is hard, some bone will be drilled out by the cutting blade 24 but will be reserved inside the indentations 13. In a preferred embodiment, the dental implant body 10 has a total of three apex indentations 13.

7 Claims, 8 Drawing Sheets

DENTAL IMPLANT

BACKGROUND OF THE PRESENT INVENTION

1. Field of Invention

The present invention relates to dental implants, and particularly to (1) a dental implant having an apex lock for better osseous integration and sinus lift, (2) a hexamaxim lock design, hex-engaging slot, for maximum friction/stability, (3) ferroembrace for additional stability/seating, (4) asymmetrical (sharp) threads providing self drilling effect/reduce resistance of bone—also called Drill Implant, (5) a cervical slop for shifting location of margin design of a restoration, (6) cervical steps for shifting location of margin design of a restoration, (7) 3 plurality of apex indentations for increasing cutting efficiency, (8) apexsinoelevation tip for elevating maxillary sinus floor.

2. Description of Related Arts

A dental implant is an artificial tooth root replacement and is used in prosthetic dentistry to support restorations that resemble a tooth or group of teeth. Multiple millions of implants have been placed to replace missing teeth per year in last 20 years. However, there are still many problems regarding to safety, patients comfort, prognosis, esthetics and cost which results in only less than 3% of dentists provide this service to patients and less than 5% of the patients who really need dental implants service receiving this service. Further, there were some permanent nerve damage occurred during implant surgery.

Therefore, design of a new dental implants become very important to (1) increase safety, (2) shorten the period of osseousintegration, (3) reduce the time of treatment, (4) reduce the cost of implant dentistry, (5) increase successful rate, (6) improve patient comfort, (7) improve esthetics and function. The more important issue is to encourage dentists and dental specialists to provide this service to their patients by developing a new implant design, which can reduce nerve damage arising out of dental implant related surgery, increase primary stability, reduce surgical trauma to patients, shorten surgical time/time for restoration, increase quantity/quality of osseousintegration, avoid additional bone graft procedures, increase stability and surface contact between implant, abutment and screw to avoid post restoration failure and reduce the issue of technique sensitive.

SUMMARY OF THE PRESENT INVENTION

A main object of the present invention is to provide a dental implant which is increasing quantity and quality of osseous-integration.

Another object of the present invention is to provide a dental implant which is convenient to be placed and reduces the issue of technique sensitive.

Another object of the present invention is to provide a dental implant which gains maximum primary stability.

Another object of the present invention is to provide a dental implant to increase the preservation of bone.

Another object of the present invention is to provide a dental implant to prevent implant rotation after operation.

Another object of the present invention is to provide a dental implant to prevent the screw loose from the abutment, which is a major issue of post treatment failure.

Another object of the present invention is to provide a dental implant to increase the successful rate of operation, to avoid multiple surgeries and to improve esthetics and function.

Another object of the present invention is to shorten the time of surgery, restoration, and treatment period.

Another object of the present invention is to allow shifting location of margin design.

Another object of the present invention is to avoid injuring dental alveolar nerve by leaving cervical slop portion supragingivally.

Accordingly, in order to accomplish the above objects, the present invention provides a dental implant, comprising:

a dental implant body;

an apex lock for locking on the apical part of the implant;

3 plurality of apex indentations a apexsinoelevation tip on apical end of the implant;

a hexamaxim lock inside the dental implant body for maximizing friction between abutment and the implant;

an asymmetric thread on the outer wall of the middle portion and spiral shaping edge on the outer wall of apical portion of the dental implant body;

ferroembrace to provide additional seating/stability and esthetics; and a cervical slop for shifting location of margin design of a restoration;

OR cervical steps for shifting location of margin design of a restoration.

These and other objectives, features, and advantages of the present invention will become apparent from the following detailed description, the accompanying drawings, and the appended claims.

DETAILED DESCRIPTION OF THE PREFERRED EMBODIMENT

Figure 1:
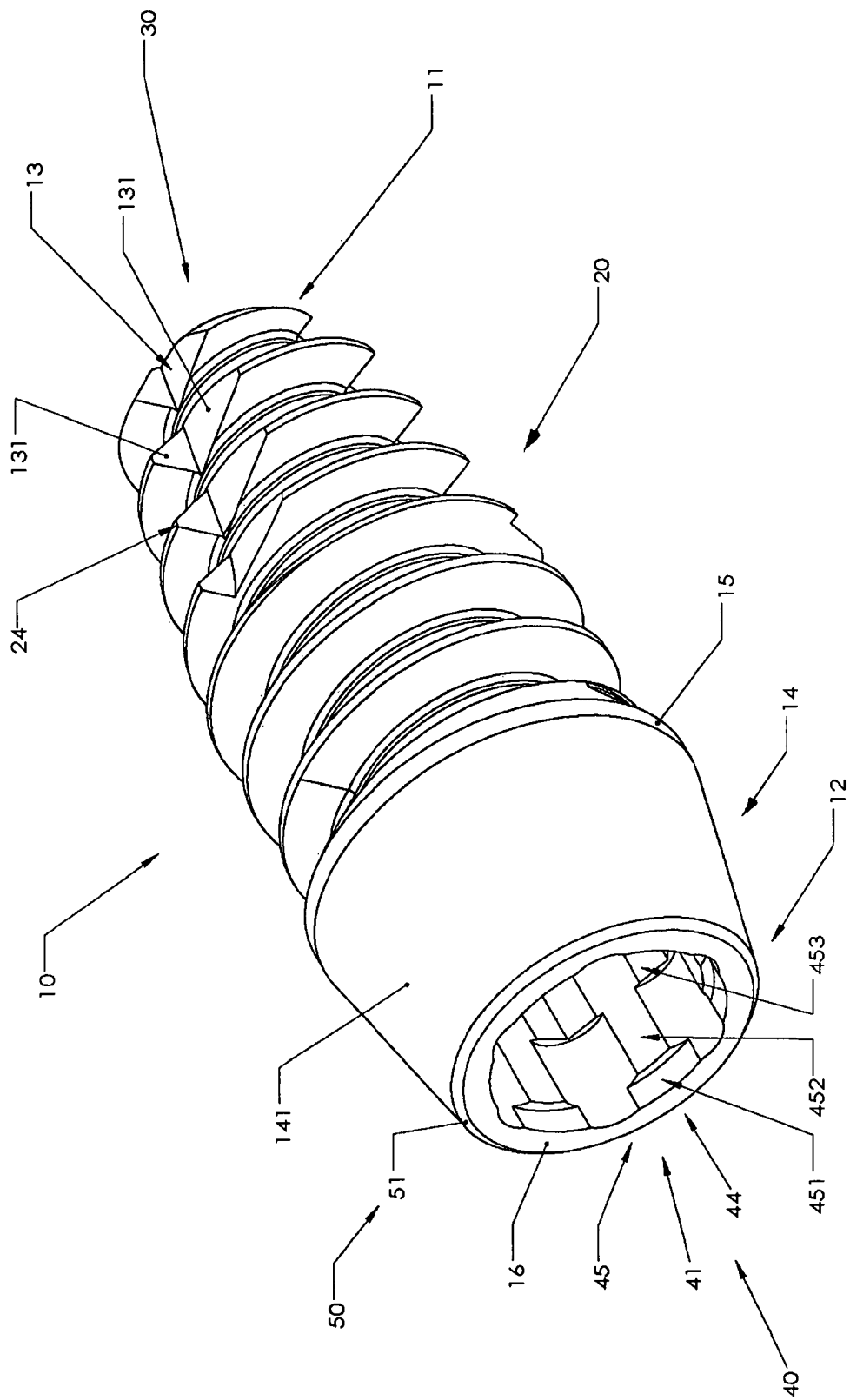
FIG. 1 is a perspective view of a dental implant according a preferred embodiment of the present invention.
Figure 2:
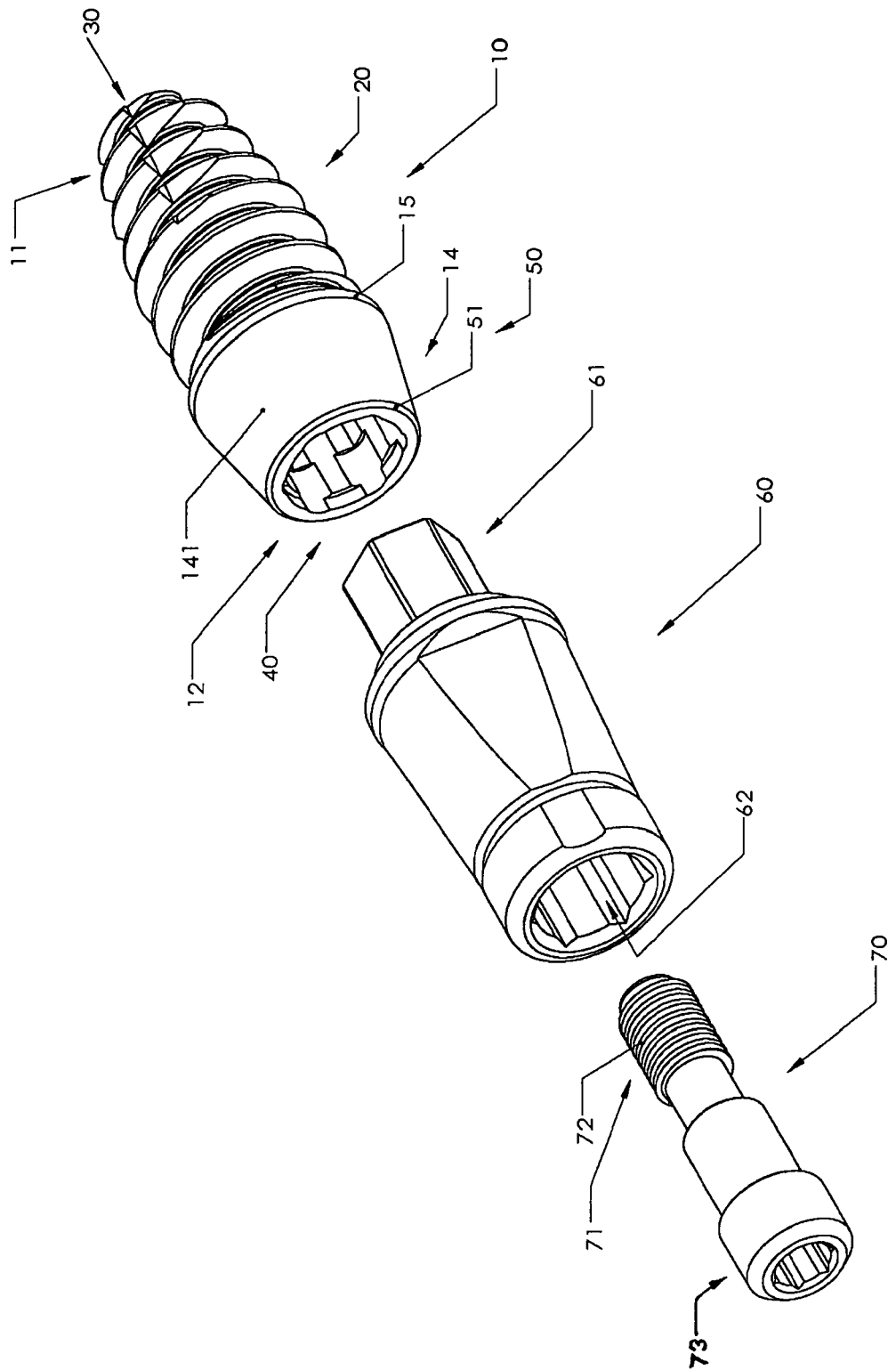
FIG. 2 is an exploded view illustrating a dental implant, an abutment and a bolt for securing the abutment with the dental implant according to above preferred embodiment of the present invention.
Figure 3:
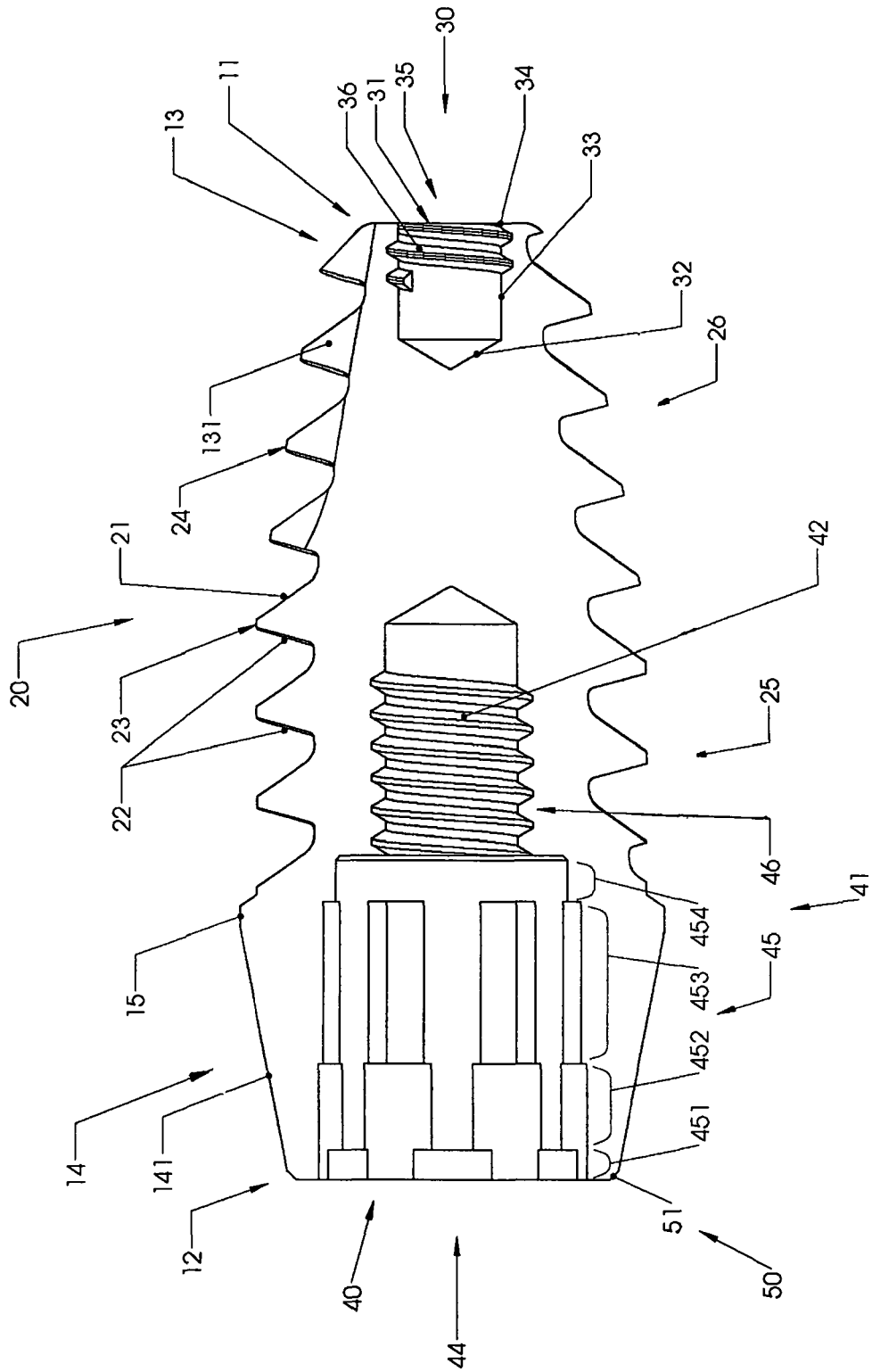
FIG. 3 is a sectional view of the dental implant according to the above preferred embodiment of the present invention.

Referring FIGS. 1 to 3 of the drawings, a dental implant according to a preferred embodiment of the present invention is illustrated, wherein the dental implant comprises a dental implant body 10 which is an irregular cylinder body having a first end 11 for inserting into the bone of the desired position and a second end 12 for integrally connected with an abutment 60 through a bolt 70, wherein an asymmetric thread 20 is provided around the dental implant body 10, an apex lock 30 is formed at the first end, and a hexamaxim lock 40 is provided at the second end.

The dental implant body 10 has a circular cross section extended between the first end 11 and the second end 12 and a tapered insertion root portion adjacent the first end 11, enabling the dental implant to be more easily inserted into the bone. The second end 12 consists of the ferroembrace 50 and platform 16. The platform 16 is the uppermost portion of the dental implant 10. An abutment will seat on the platform 16. The second end 12 of the dental implant body 10 is designed to be placed supragingivally or subgingivally for connecting with abutment 60. A cervical slop or cervical steps located between the second end 12 and asymmetric thread 20 is designed to allow restorative dentist to shift margin design. The dimension, including the length and the diameter, of the dental implant body 10 varies according to different sinus situation.

The asymmetric thread 20 is integrally formed around an outer wall of the dental implant body 10 and extending from the 360° flat surface 15 to the first end 11 thereof. The asymmetric thread 20 is a continued thread, or, alternatively discontinued in multiple segments, adapted to screw into the bone of the sinus and be retained by the bone steadfastly.

Referring to FIG. 3, since symmetric thread is not efficient enough for a dental implant, the asymmetric thread 20 of the present invention is made asymmetrical that the two sides of the thread have different slope angles. As illustrated in the cross sectional view of FIG. 3, the asymmetric thread 20 has a first side 21 and a second side 22. The first side, which is facing the first end 11 of the dental implant body 10, has a smaller slope angle while the second side 22, which is facing the second end 12 of the dental implant body 10, has a larger slope angle, so that the second side 22 is more precipitous than the first side 21. Since the slope angle of the first side 21 is smaller, it has less resistance when the dental implant is inserted into the sinus. In contrast, since the slope angle of the second side 22 is larger, it has larger resistance to pull the dental implant out of the alveolar bone. Accordingly, the asymmetric thread 20 is more efficient to be inserted into the alveolar bone and increases the initial stability of the implant after the operation.

Figure 4:
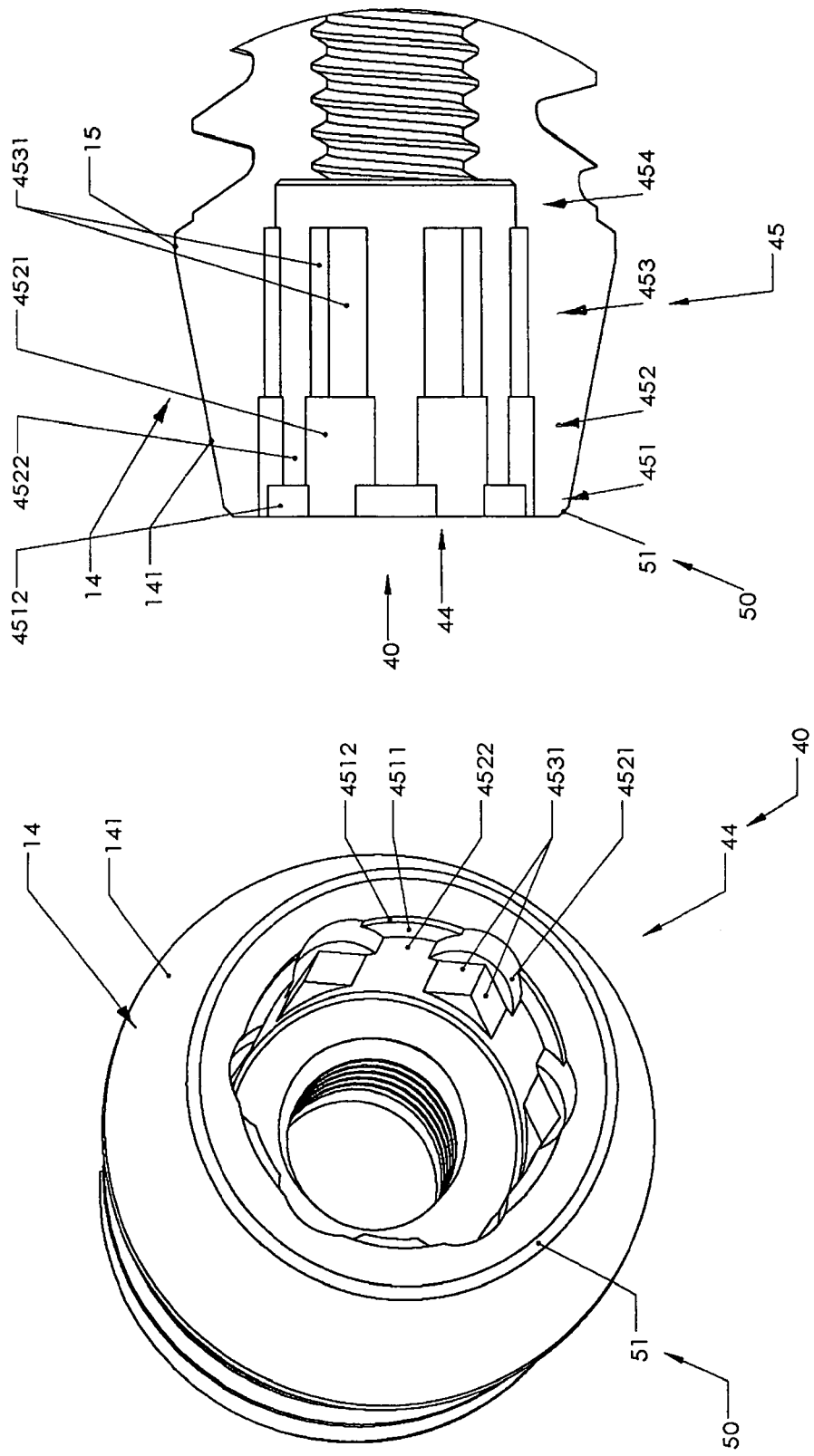
FIG. 4 is a detail view of the hexamaxim lock cavity of the dental implant according to the sectional view above of the present invention.
Figure 7:
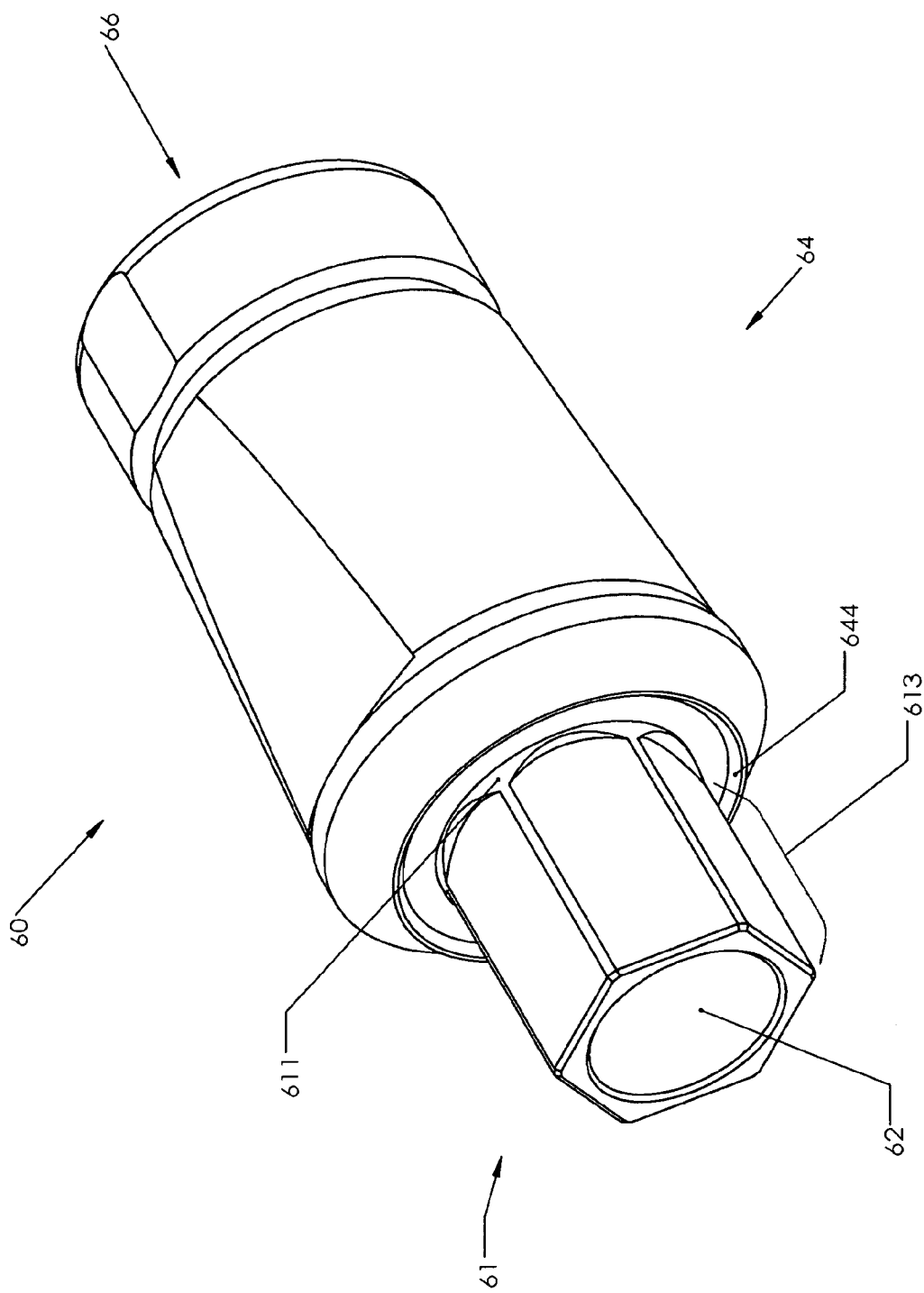
FIG. 7 is a perspective view of a fixture mount abutment according to a preferred embodiment of the present invention.

Referring to FIGS. 3, 4 & 7, the detail views of the first section 45 of the hexamaxim lock cavity 44 of dental implant is illustrated. The wall of hexamaxim lock cavity consists of 4 layers of retentive features. The first layer 451 which is closely adjacent to platform 16 is formed by 6 flat platforms 4511 and 6 curved vertical walls 4512 at an angle of 90°. The first layer of retentive feature 451 is designed to engage with the wave-shaped protruded feature 611 in the abutment which can tremendously enhance the stability of the implant and abutment. The second layer 452 consists of 6 vertical lobes 4521 with 6 curved vertical surfaces 4522 which extend 1.20 mm to 1.30 mm in depth. The third layer 453 contains 6 curved vertical surfaces and between every two of which is 1 pair of 120° angled flat surfaces 4531 with a total of 6 pairs of 120° angled flat surfaces. The fourth layer 454 is a 360° rounded channel wall.

Regarding hardness of bone which can be divided into 4 types, type 1 represents the hardest bone and Type 4 represents the softest bone. Referring to FIGS. 1 to 3, the asymmetric thread 20 also structured to have a blade edge 23 at a tip between the first and second sides 21, 22. The blade edge 23 can acts as self cutting edge which can easily cut into the bone of Types 3 and 4, or has less resistance for bone or Types 1 and 2. When the dental implant is screwed into the sinus where the bone is Type 3 or 4, the sharpened blade edge 23 can cut into the surrounding bone without drilling. It substantially realizes drill-less implant operation. If the bone is Type 1 or 2, much less bone is required to be drilled to insert the dental implant. This will maximally reduce the bone loss which is critical for high stability and successful rate of dental implant. Moreover, the sharpened blade edge 23 of the asymmetric thread 20 also can largely reduce the heat generated during screwing, and reduces the time for operation. Both heat and time largely affect the successful rate of operation.

In order to further facilitate the insertion of the dental implant into the bone, 3 plurality of apex indentions 13 are spacedly formed in the insertion root portion of the dental implant body 10. Referring to FIGS. 1 to 3 of the drawings, in a preferred embodiment of the present invention, each apex indentation 13 has a V-shape cross section defining two blade surfaces 131 cutting into the dental implant body 10 from the tip of the first end 11 of the dental implant body 10. At these two blade surfaces 131, the cross section of the asymmetric thread 20 is exposed and the blade edge 23 of the asymmetric thread 20 forms one or more cutting blades 24, wherein when the dental implant of the present invention is screwed in the bone, the cutting blades 24 are the first part to cut into the bone. If the bone is hard, some bone will be drilled out by the cutting blade 24 but will be reserved inside the indentations 13. In a preferred embodiment, the dental implant body 10 has a total of three apex indentations 13.

Figure 5:
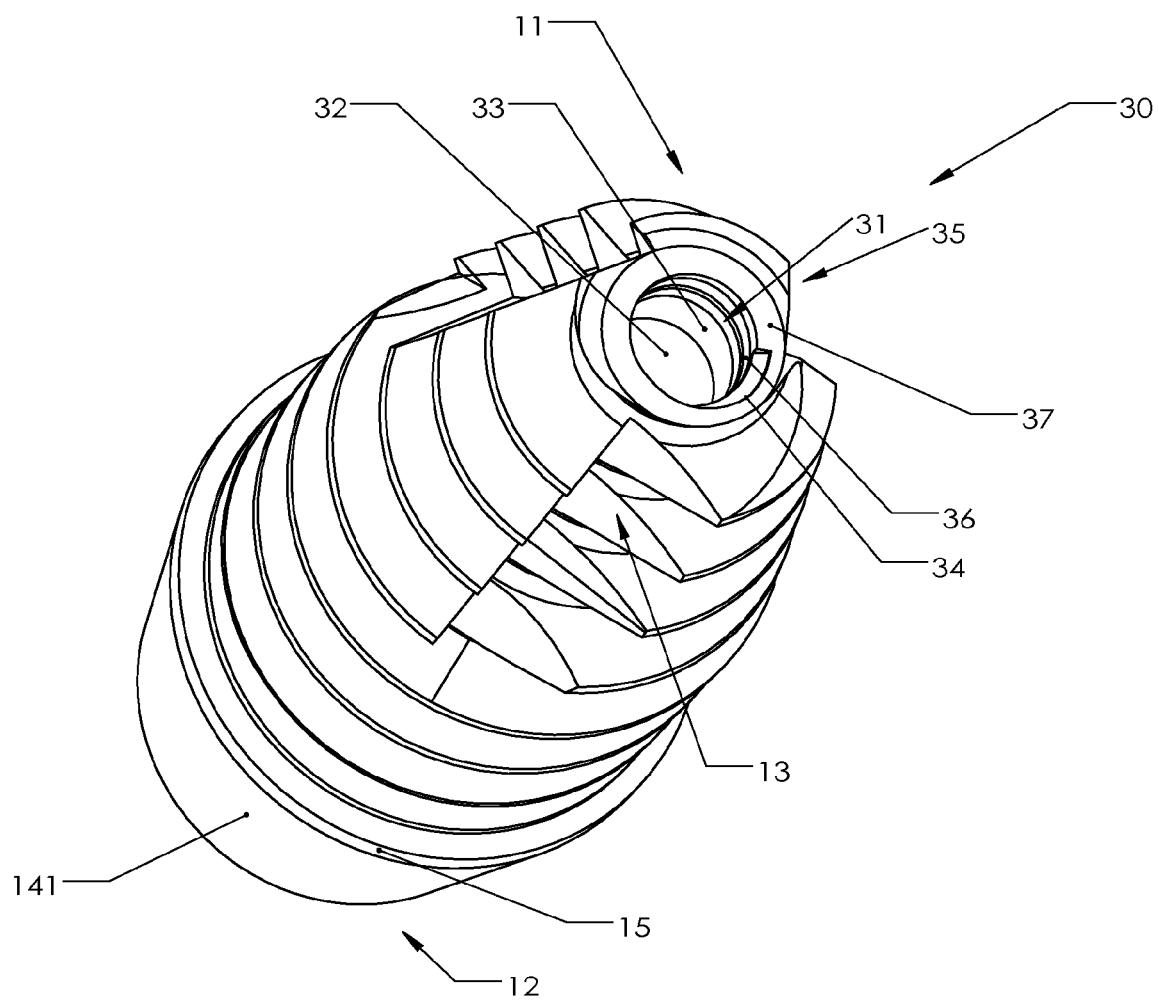
FIG. 5 is a perspective view of an alternative mode of the dental implant according to the above preferred embodiment of the present invention.

Referring to FIGS. 3 & 5, the apex lock 30 of the dental implant is provided at the first end 11 of the dental implant body 10. The apex lock 30 has an apex cavity 31 which has a cavity bottom 32 and a cavity wall 33. The cavity wall 33 extends to a periphery edge of the apex lock 30 to form a cavity edge 34. This cavity edge 34 defines an apex opening 35, allowing bone to grow into the apex cavity 31.

The apex lock 30 also comprises a lock element 36 in the apex cavity 31. The lock contains grooves or ribs provided around the cavity wall 33 to increase infliction. In a preferred embodiment, the lock element 36 is embodied as an internal thread on the cavity wall 33 of the apex cavity 31. Generally, the bone at the bottom of the bone marrow gets more blood supply after dental implantation. So at this area the surface of dental implant will have better osseous integration. The space formed in the apex cavity 31 enables the new grown bone extending into the apex cavity 31 of the apex lock 30 as well as the grooves or the grooves of the internal thread on the cavity wall 33 so as to provide a locking mechanism to ensure a long term progress of integration between the dental implant and the bone.

One of the issues that cause the failure of dental implantation most often is the loose of the implant. The dental implant could be unscrewed out of the alveolar bone before it is integrated tightly with the bone. It is worth mentioning, the internal thread of the cavity wall 33 of the apex cavity 31 is oriented in an opposite direction of the asymmetric thread 20 of the dental implant body 10. In this manner, when extra force is trying to loosen the screw of the asymmetric thread 20, it is also fastening the internal thread of the apex lock 30 at the same time. These two opposite forces will diminish each other. As a result, loosening of the implant after implantation can be avoided.

Referring to FIGS. 3 & 5, the apexsinoelevation tip 37 is a narrow platform located at the lowermost end, formed at the first end of dental implant body 10. Three indentations 13 slightly nick the peripheral edge of the apexsinoelevation tip. The apex cavity cuts through the large portion of center part of the plate form which makes the platform a thin and moderately sharp circle band. When the dental implant with the apexsinoelevation tip 37 is screwed into the sinus, the apexsinoelevation tip 37 is applied on the floor of the sinus. Because of the asymmetric thread 20, the torque is converted to linear force towards the floor of the sinus. The apexsinoelevation tip 37 will perform the bone expansion with the outer wall. At the same time, the apexsinoelevation tip 37 is going deeper into the sinus and elevates the sinus floor. With the capability of sinus lifting and bone expansion due to the apexsinoelevation tip 37, the dental implant will be retained more stably.

Referring to FIGS. 1 to 4 & 7, the hexamaxim lock 40 of the dental implant of the present invention is for housing the abutment 60. The hexamaxim lock 40 provides a lock cavity 41 and a lock thread 42. The lock cavity 41 has a lock opening 44 at the second end 12 of the dental implant body 10, and extends longitudinally inside the dental implant. The lock cavity 41 has two sections. The first section 45 of the lock cavity 41 is close to the lock opening 44. This section is designed to harbor the hex-shaped root 61 of the abutment 60 and the angled flat surfaces 4531 within this section are loosely fitting to the hex-shaped body 613 of the abutment 60.

Figure 8:
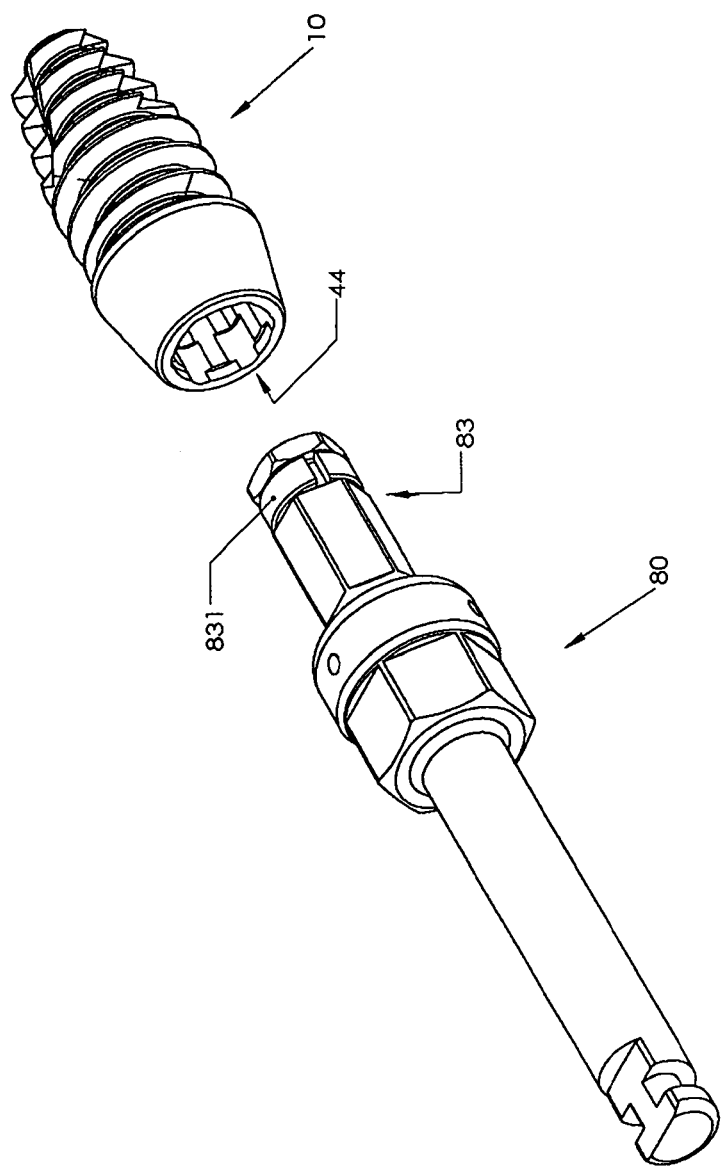
FIG. 8 is an exploded view illustrating a dental implant and a fixture mount driver for securing the implant into the bone according to above preferred embodiment of present invention.

Referring to FIGS. 4 & 8, the first section 45 of the lock cavity 41 is also designed to receive the hex cylinder shank 83 of the fixture mount driver 80. The angled flat surfaces 4531 are loosely fitting to the hex cylinder shank 83. However, the snap ring 831 attached to hex cylinder shank 83 is tightly fitting to the angled flat surfaces 4531 so as to pick up and place dental implant 10 into alveolar bone during dental implant surgery.

The second section 46 which is adjacent to the first section 45 is located deeper inside the lock cavity 41. The lock thread 42 is provided around the inner wall of the second section. This lock thread 42 is adapted to be screwed with the bolt 70. After a dental implant is secured inside the bone, the abutment 60 is ready to be mounted. First, the hex-shaped root 61 of the abutment 60 is inserted into the first section 45 of the lock cavity 41. Then the abutment 60 is fastened onto the dental implant through the bolt 70. The abutment 60 has a through hole 62 communicating the lock opening 44 and the second section of the lock cavity 41. A tip 71 of the bolt 70 having an external thread 72 is adapted to pass through the through hole 62 of the abutment 60 and screw with the lock through of the dental implant. A head 73 of the bolt 70 remains in the through hole 62 of the abutment 60 for driving the bolt 70 and retaining the abutment 60. In this manner, the bolt 70 and the dental implant body 10 have a metal to metal contact which is very stable. This can steadily fasten the abutment 60 onto the dental implant 10. The stability is largely increased.

It is worth mentioning that the conventional dental implant generally has only three internal engaging portions for engaging with three engaging jaws of the conventional abutment, wherein the abutment 60 has to be rotated 120° to get to the next secure position and there are only three secured positions to choose from. This is very inconvenient to place the abutment with a suitable rotary angle especially when the root of the abutment has an angle. According to the preferred embodiment of the present invention, the third layer of the first section 45 of the lock cavity 41 has 6 pairs of 120° angles flat surfaces 4531 distributed evenly around the axle of the dental implant 10. So that the angle is 60° rotating from one engaging slot 4531 to the next engaging slot 4531 and the abutment 60 has six secured positions to choose from while the prior art dental implant merely contains three secured positions to choose from. In other words, the prior art dental implant needs to be rotated 120° to find the next secured position and the dental implant of the present invention enables the dentist to simply rotate it for 60° for the next secured position. It is much flexible to find a suitable rotary angle for easy alignment of the dental crown.

(1) In many cases, since some maxillary sinuses are pneumatized, there is not enough vertical dimension to accommodate the full body length of a dental implant, (2) or, in other cases, alveolar nerve can be very closely to alveolar crest, where there is not enough vertical dimension to house the full dental implant. In this situation, dentist can leave cervical slop 14 or cervical steps 17 supragingivally to avoid intruding or damaging the underlying nerve tissue.

Referring to FIGS. 1, 3, 4 & 6, the dental implant body 10 has a cervical slop 14 or cervical steps 17 provided between ferroembrace 50 and the 360° flat surface 15. The cervical slop 14 is a taper wall 141 extending upwardly from the 360° flat surface 15 to ferroembrace 50 in a taper manner. The cervical slop 14 attenuates the second end 12 of the dental implant body 10; while slightly increases the diameter of the profile. The cervical slop 14 can be a smooth surface, rough surface or threaded surface.

Figure 6:
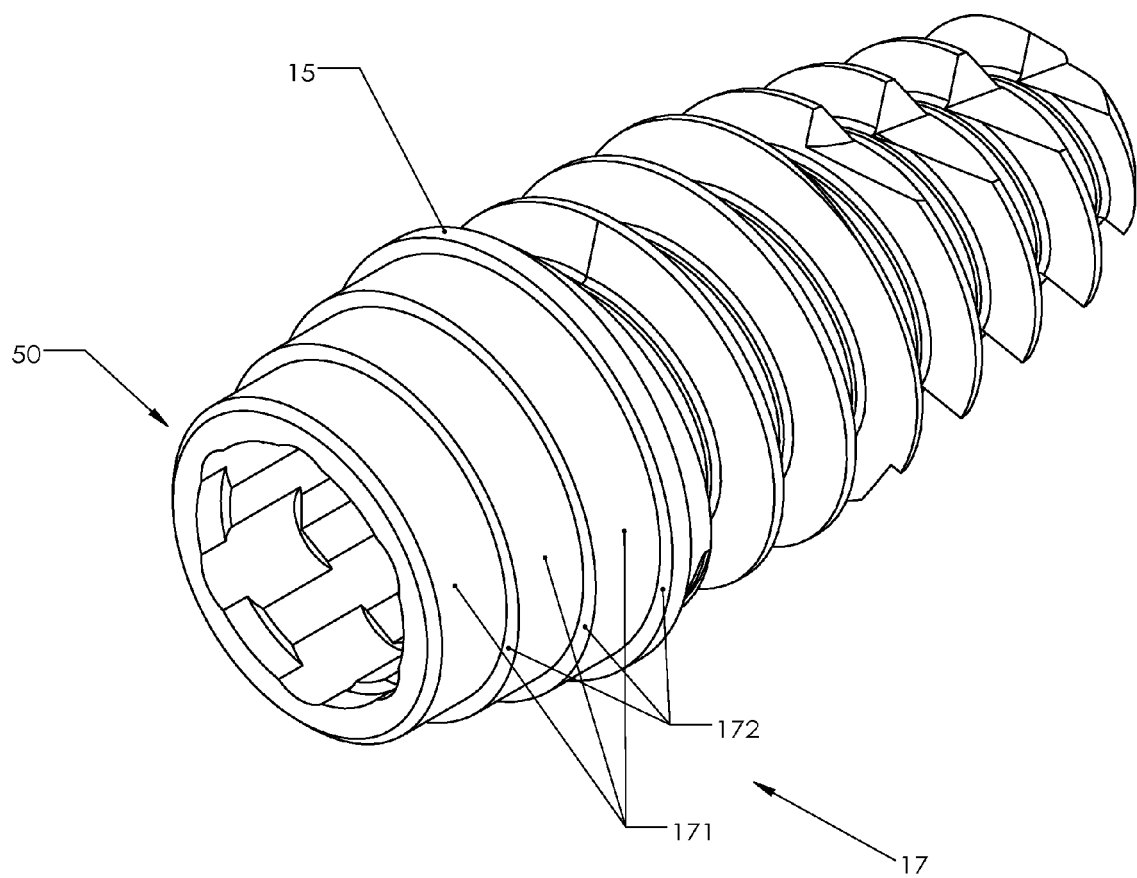
FIG. 6 is a perspective view of the alternative version of the present dental implant design with cervical steps.

What is shown in FIG. 6 is an alternative version of dental implant with cervical steps 17. The cervical steps 17 consists of multiple step surfaces 172 and multiple taper surfaces 171. Instead of cervical slop 14, this version of dental implant can have 2~6 steps distributed between ferroembrace 50 and 360° flat surface 15. The thickness of each step varies from 0.1 mm to 0.5 mm, and the angle between each taper surface 171 and its adjacent step surface 172 varies from 45° to 150°. The cervical steps 17 would slightly attenuate the second end 12 of the dental implant. However, it can allow the bone to have more space to grow into and have better osseousintegration. The purpose of the cervical slop 14 or cervical steps 17 is designed for esthetics, retention and safety reasons. The cervical slop 14 or cervical steps 17 allow clinician to shift the margin of the restoration/crown more apically to improve esthetics in case that the implant body 10 is exposed supragingivally due to tissue resorption, technical issue or safety reason. In many clinical cases, there is not enough vertical height of alveolar bone to anchor the dental implant body 10. In order to avoid the dental implant body 10 from injuring a dental alveolar nerve or underlying tissue, clinician can choose to leave the cervical slop 14 or cervical steps 17 supragingivally. Then the exposed portion of the cervical slop 14 or cervical steps 17 can be covered by a ceramic crown/restoration, which is a tooth shade to improve esthetics. The cervical slop 14 or cervical steps 17 of the present invention helps a surgeon to control the depth of a dental implant 10 to be inserted. By designing the feature of the cervical slop 14 or cervical steps 17, the chance of injury of alveolar nerve can be largely reduced. Since injury of alveolar nerve is a large portion of dental malpractice claim, the cervical slop 14 and cervical steps 17 can largely increase safety of dental implant surgery. In addition, by placing margin of restoration more apically, the retention can be substantially increased. Further, where the cervical slop 14 or cervical steps 17 is placed subgingivally or infrabony (below the alveolar bone), the cervical slop 14 or cervical steps 17 will allow alveolar bone integrating on the slop surface 141 of cervical slop 14 or step surfaces 171 and steps surfaces 172 of cervical steps 17, which can further stabilize the dental implant body 10 to resist dislodging, extracting, bending and pulling force. The longevity of dental implant and restoration can be substantially improved.

Referring to FIG. 1 to 5, the dental implant body 10 further has a ferroembrace 50 provided around the second end 12 thereof. The ferroembrace 50 is a bevel 51 extending inwardly from the periphery edge of the second end 12 of the dental implant body 10. The ferroembrace 50 thickens the second end 12 of the dental implant body 10 while slightly decreases the diameter of the profile. The purpose of the ferroembrace 50 design is for esthetics and retention reasons. If the depth of dental implant inserted into the bone is too shallow, the metal of the implant body will be exposed which is not esthetic. The ferroembrace 50 of the present invention helps the surgeon to control the depth of the dental implant to be inserted. During the surgery, the gum should be placed on the bevel 51 of the ferroembrace 50. In this manner, the gum tissue is healthier and thicker, less metal of the dental implant body 10 is exposed, and the stability of the dental implant is increased. In addition, porcelain margin of a restoration can be used to cover the exposed bevel to improve esthetics and restoration.

Referring to FIGS. 2, 3, 4 & 7, as the hex-shaped root 61 of the abutment 60 is inserted into the lock cavity 41 of the dental implant 10, the first layer of retentive feature 451 will be engaged by the wave-shaped protruded feature 611 in the abutment, while the ferro 644 of the abutment 60 will also be engaging the bevel 51 of the dental implant. These two additional retentive features together can dramatically enhance the stabilization between abutment 60 and dental implant 10.

In summary, the present invention is a self-drilling and drill-less dental implant. It utilizes asymmetric thread 20 to ease the implant surgery and increase the stability of the integration. The blade edge 23 and the cutting blades 24 of the asymmetric thread 20 maximally preserved the bone during screwing. The apex lock 30 provides the apex cavity 31 so that the bone can grow into it. The internal thread 36 increases the friction so the bone can integrate with the dental implant in more stable manner. Also the internal thread 36 has an opposite direction of the asymmetric thread 20 which prevents the implant from loosing. The apex lock 30 can also have an apexsinoelevation tip 37 adapted to perform sinus lifting during the operation of dental implantation.

The present invention also provides a hexamaxim lock 40 providing metal to metal contact to secure the abutment 60 onto the dental implant body 10. The first section 45 of the lock cavity 41 provides more slots to increase the flexibility for securing and alignment. The cervical slop 14 and cervical steps 17 of the present invention help a surgeon to control the depth of the dental implant to be inserted. Further, the cervical slop or cervical steps will allow alveolar bone integrating on the slop surface 141 or the cervical steps 17, which can further stabilize the dental implant body 10. The ferroembrace helps the surgeon to control the implant position, retention of restoration and reduces the metal exposure.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A dental implant, comprising:
a dental implant body which is a cylindrical body having a first end, a second end, a 360° flat surface between said first and second ends of said dental implant body, an asymmetric thread formed around an outer wall of said dental implant body and extended from said flat surface of said dental implant body to said first end of said dental implant body, an apexsinoelevation tip formed at a first end of said dental implant body, and a cervical slope located between said second end of said dental implant body and said asymmetric thread of said dental implant body, a hexamaxim lock being provided at said second end of said dental implant body for connecting with an abutment through a bolt, and an apex lock formed at said first end of said dental implant body, wherein said apex lock has an apex cavity which has a cavity bottom and a cavity wall which extends to a periphery edge of said apex lock to form a cavity edge which defines an apex opening, wherein said apex lock comprises a lock element in said apex cavity, wherein said lock element which is an internal thread provided on said cavity wall of said apex cavity, wherein said internal thread of said cavity wall of said apex cavity is oriented in an opposite direction of said asymmetric thread, wherein said second end of said dental implant body has a ferroembrace and a platform which is an uppermost portion of said dental implant body, wherein said ferroembrace is a bevel extending inwardly from a periphery edge of said second end of said dental implant body for thickening said second end of said dental implant body, wherein said asymmetric thread of said dental implant body has a first side and a second side having different slope angles, wherein said first side which is facing said first end of said dental implant body having a smaller slope angle while said second side which is facing said second end of said dental implant body having a larger slope angle, wherein said asymmetric thread has a tapered insertion root portion adjacent to said first end of said dental implant body, wherein said tapered insertion root portion has a plurality of apex indentations which are spacedly formed therein, wherein each of said plurality of apex indentations has a V-shape cross section defining two blade surfaces cutting into said dental implant body from a tip of said first end of said dental implant body, wherein a cross section of said asymmetric thread is exposed and said blade surfaces of said asymmetric thread forms cutting blades, wherein said apexsinoelevation tip is a narrow platform located at a lowermost portion of said first end of said dental implant body, wherein said plurality of apex indentations slightly nick a peripheral edge of said apexsinoelevation tip, wherein said apex cavity cuts through a large portion of a center part of said narrow platform making said narrow platform a thin and moderately sharp circle band, wherein said cervical slope, which is provided between said ferroembrace and said flat surface, is a taper wall extending upwardly from said flat surface to said ferroembrace in a taper manner such that a diameter size of said second end is smaller than a diameter size of said flat surface, wherein said cervical slope, which has a slope surface, attenuates said second end of said dental implant body while slightly increasing a diameter thereof, thereby when a force is applied to loosening said asymmetric thread, said internal thread of said apex lock is fastened at the same time.

2. The dental implant, as recited in claim 1, wherein said hexamaxim lock has a hexamaxim lock cavity defining a lock opening at said second end of said dental implant body and extending longitudinally inside thereof, wherein a wall of said hexamaxim lock cavity has a first layer formed by six flat platforms and six curved vertical walls, a second layer having six vertical lobes with six curved vertical surfaces, a third layer having six curved vertical surfaces and between every two of said six curved vertical surfaces is one pair of 120° angled flat surfaces with a total of six pairs of 120° angled flat surfaces, and a fourth layer forming a 360° rounded channel wall.

3. The dental implant, as recited in claim 2, wherein each of said six curved vertical surfaces of said second layer extends 1.2 mm to 1.3 mm in depth.

4. The dental implant, as recited in claim 1, wherein said taper wall has a slope surface selected from the group consisting of smooth surface, rough surface and thread surface.

5. A dental implant, comprising:

a dental implant body which is a cylindrical body having a first end, a second end, a 360° flat surface between said first and second ends of said dental implant body, an asymmetric thread formed around an outer wall of said dental implant body and extended from said flat surface of said dental implant body to said first end of said dental implant body, an apexsinoelevation tip formed at a first end of said dental implant body, and cervical steps located between said second end and said asymmetric thread of said dental implant body, a hexamaxim lock being provided at said second end of said dental implant body for connecting with an abutment through a bolt, and an apex lock formed at said first end of said dental implant body, wherein said apex lock has an apex cavity which has a cavity bottom and a cavity wall which extends to a periphery edge of said apex lock to form a cavity edge which defines an apex opening, wherein said apex lock comprises a lock element in said apex cavity, wherein said lock element which is an internal thread provided on said cavity wall of said apex cavity, wherein said internal thread of said cavity wall of said apex cavity is oriented in an opposite direction of said asymmetric thread, wherein said second end of said dental implant body has a ferroembrace and a platform which is an uppermost portion of said dental implant body, wherein said ferroembrace is a bevel extending inwardly from a periphery edge of said second end of said dental implant body for thickening said second end of said dental implant body, wherein said asymmetric thread of said dental implant body has a first side and a second side having different slope angles, wherein said first side which is facing said first end of said dental implant body having a smaller slope angle while said second side which is facing said second end of said dental implant body having a larger slope angle, wherein said asymmetric thread has a tapered insertion root portion adjacent to said first end of said dental implant body, wherein said tapered insertion root portion has a plurality of apex indentations which are spacedly formed therein, wherein each of said plurality of apex indentations has a V-shape cross section defining two blade surfaces cutting into said dental implant body from a tip of said first end of said dental implant body, wherein a cross section of said asymmetric thread is exposed and said blade surfaces of said asymmetric thread forms cutting blades, wherein said apexsinoelevation tip is a narrow platform located at a lowermost portion of said first end of said dental implant body, wherein said plurality of apex indentations slightly nick a peripheral edge of said apexsinoelevation tip, wherein said apex cavity cuts through a large portion of a center part of said narrow platform making said narrow platform a thin and moderately sharp circle band, wherein said cervical steps have step surfaces and taper surfaces distributed between said ferroembrace and said flat surface, wherein a thickness of each of said cervical steps is 0.1 mm to 0.5 mm and an angle between each of said taper surfaces and one of said step surface adjacent thereto is 45° to 150°, wherein said cervical steps attenuate said second end of said dental implant thereby when a force is applied to loosening said asymmetric thread, said internal thread of said apex lock is fastened at the same time.

6. The dental implant, as recited in claim 4, wherein said hexamaxim lock has a hexamaxim lock cavity defining a lock opening at said second end of said dental implant body and extending longitudinally inside thereof, wherein a wall of said hexamaxim lock cavity has a first layer formed by six flat platforms and six curved vertical walls, a second layer having six vertical lobes with six curved vertical surfaces, a third layer having six curved vertical surfaces and between every two of said six curved vertical surfaces is one pair of 120° angled flat surfaces with a total of six pairs of 120° angled flat surfaces, and a fourth layer forming a 360° rounded channel wall.

7. The dental implant, as recited in claim 6, wherein each of said six curved vertical surfaces of said second layer extends 1.2 mm to 1.3 mm in depth.

* * * * *